United States Patent [19]

O'Brien et al.

[11] Patent Number: 5,731,391

[45] Date of Patent: Mar. 24, 1998

[54] FLUID COMPOSITION FOR PHYSIOLOGICAL SEPARATIONS WITH ENHANCED RESISTANCE TO INWARD MIGRATION OF SUBSTANCES REQUIRING ACCURATE DOSAGE MONITORING

[75] Inventors: William L. O'Brien, Cincinnati; Alan C. Kilbarger, Milford, both of Ohio

[73] Assignee: Henkel Corporation, Plymouth Meeting, Pa.

[21] Appl. No.: 722,913

[22] Filed: Sep. 27, 1996

[51] Int. Cl.$^6$ .................................................. C08F 20/00
[52] U.S. Cl. .................. 525/444; 528/295.3; 528/297; 528/300; 528/301; 528/302; 528/303; 528/306; 528/308; 528/308.6; 525/437; 525/444; 525/445; 525/446; 525/447; 210/782; 210/789
[58] Field of Search .................................. 528/295.3, 297, 528/300, 301, 302, 303, 306, 308, 308.6; 525/437, 444, 445, 446, 447; 210/782, 789; 524/442

[56] References Cited

U.S. PATENT DOCUMENTS

| | | | |
|---|---|---|---|
| 4,101,422 | 7/1978 | Lamont | 210/789 |
| 4,426,290 | 1/1984 | Ichikawa | 210/516 |
| 4,994,393 | 2/1991 | Pradhan | 436/8 |
| 5,124,434 | 6/1992 | O'Brien | 528/272 |

OTHER PUBLICATIONS

A.Y. Coran et al., Rubber Chem. Technol., 56, 1045 (1983).
P. Orsulak et al., Therapeutic Drug Monitoring, 6:444–48 (1984).
Y. Bergqvist et al., Clin. Chem., 30:465–66 (1984).

*Primary Examiner*—Samuel A. Acquah
*Attorney, Agent, or Firm*—Ernest G. Szoke; Wayne C. Jaeschke; John E. Drach

[57] ABSTRACT

A fluid which comprises an olefin-terminated polyester an unmodified polyester and a polymerized α-olefin is provided which facilitates the separation of blood into light and heavy phases via centrifugation in a blood collection vessel. The fluid is useful as a component of a partitioning composition formulated to have appropriate specific gravity to be positioned intermediate the light and heavy blood phases during centrifugation. A partitioning composition including a fluid of the invention provides a particular advantage in blood collection vessels used in therapeutic drug monitoring, due to the relatively low affinity between the fluid component of the composition and commonly monitored classes of drugs.

42 Claims, No Drawings

FLUID COMPOSITION FOR PHYSIOLOGICAL SEPARATIONS WITH ENHANCED RESISTANCE TO INWARD MIGRATION OF SUBSTANCES REQUIRING ACCURATE DOSAGE MONITORING

FIELD OF THE INVENTION

The present invention relates to fluids useful for facilitating physiological separations, such as of blood serum or plasma from the cellular portion of blood.

BACKGROUND OF THE INVENTION

The fluids of the invention are conveniently formulated into a partitioning composition for use in a blood collection vessel in which the blood sample is subjected to centrifugation until the cellular portion and serum or plasma are completely separated.

Note that while blood is the most usual candidate for physiological separation, conceivably urine, milk, sputum, stool solutions, meconium, pus and the like could all be subject to physiological separation and assay for therapeutic agents and the subsequent discussion, while focusing on blood for clarity, is not meant to be limited to blood.

The physical and chemical properties of the partitioning composition are such that a continuous, integral seal is provided between the separated blood phases, thereby maintaining separation of the phases after centrifugation and simplifying removal of the serum or plasma from the blood collection vessel. The high volume testing of blood components in hospitals and clinics has led to the development of various devices to simplify the collection of blood samples and preparation of the samples for analysis. Typically, whole blood is collected in an evacuated, elongated glass tube that is permanently closed at one end and sealed at the other end by a rubber stopper having a diaphragm which is penetrated by the double-tipped cannula used to draw the patient's blood. After the desired quantity of blood is collected, the collection vessel is subjected to centrifugation to yield two distinct phases comprising the cellular portion of the blood (heavy phase) and the blood serum or plasma (light phase). The light phase is typically removed from the collection vessel, e.g., via pipette or decantation, for testing.

It has been proposed heretofore to provide manufactured, seal-forming members, e.g., resilient pistons, spools, discs and the like, in blood collection vessels to serve as mechanical barriers between the two separated phases. Because of the high cost of manufacturing such devices to the close tolerances required to provide a functional seal, they have been supplanted by fluid sealant compositions. Fluid sealant compositions are formulated to have a specific gravity intermediate that of the two blood phases sought to be separated, so as to provide a partition at the interface between the cellular and serum phases. Such compositions typically include a polymer base material, one or more additives for adjusting the specific gravity and viscosity of the resultant composition, and optionally, a network former. Representative fluid sealant compositions developed in the past include: styrene beads coated with an anti-coagulant; silicone fluid having silica dispersed therein; a homogenous, hydrophobic copolyester including a suitable filler, e.g., silica; a liquid α-olefin-dialkylmaleate, together with an aliphatic amine derivative of smectite clay or powdered silica; the reaction product of a silicone fluid with a silica filler and a network former; and a mixture of compatible viscous liquids, e.g., epoxidized vegetable oil and chlorinated polybutene, and a thixotropy-imparting agent, e.g., powdered silica, and liquid polyesters.

Ideally, a commercially useful blood partitioning composition should maintain uniform physical and chemical properties for extended time periods prior to use, as well as during transportation and processing of blood samples, readily form a stable partition under normal centrifugation conditions and be relatively inert or unreactive toward the substance(s) in the blood whose presence or concentration is to be determined.

Inertness to substances sought to be determined is a particular concern when blood collection vessels are used for therapeutic drug monitoring (TDM), which is assuming an increasingly important role in drug treatment strategies. TDM enables the administration of drugs in the appropriate therapeutic ranges, established through the accumulated experience of clinicians, and consequently reduces the number of patients receiving dosage levels that are either below detection limits or toxic. Administration of drugs under TDM allows one to take into account such factors as drug tolerance developed with passage of time, presence of multiple physical disorders and synergistic or antagonistic interactions with other therapeutic agents. Among the drugs recommended for administration under TDM are those having dangerous toxicity with poorly defined clinical endpoint, steep dose-response curve, narrow therapeutic range, considerable inter-individual pharmacokinetic variability or non-linear pharmacokinetics, as well as those used in long term therapy or in the treatment of life-threatening diseases. By way of example, the evaluation of blood levels of a number of tricyclic antidepressant compounds, such as imipramine or desipramine, in relation to an empirically established therapeutic range is reported to be particularly useful in the treatment of seemingly drug-refractive depression. TDM is likewise used to monitor the dosage of anticonvulsant drugs, such as phenytoin and phenobarbital which are administered in the treatment of epilepsy, antitumor drugs, such as methotrexate, and other more commonly prescribed drugs, including, but not limited to digoxin, lidocaine, pentobarbital and theophylline.

Reports of recent studies on the effect of blood partitioning compositions on drug concentrations in serum and plasma indicate that care must be taken in the selection of polymeric materials which come into contact with the blood samples obtained for drug assay. See, for example, P. Orsulak et al., *Therapeutic Drug Monitoring*, 6:444–48 (1984) and Y. Bergquist et al. *Clin. Chem.*, 30:465–66 (1984). The results of these studies show that the blood partitioning compositions provided in blood collection vessels may account for reduced serum or plasma values, as a result of drug absorption by one or more components of the composition. The reported decreases in measured drug concentrations appears to be time-dependent. One report concludes that the observed decreases in drug concentrations may effectively be reduced by minimizing the interval between collection and processing. Another report recommends that blood samples be transported to the laboratory as soon as possible, with processing occurring within 4 hours. A commercially useful blood collection vessel, however, must produce accurate test results, taking into account routine clinical practices in large institutions, where collection, transportation and processing of blood samples may realistically take anywhere from about 1–72 hours.

Conventional polyester fluids are inadequate penetration barriers and therapeutic agents will diffuse into them and be partially absorbed with time, which interferes with quantitative assay for their presence. Attempts to solve this problem have centered around techniques for making the polyester itself more hydrophobic. Most therapeutic agents have high solubility parameters and associated high hydrophilicity (associated with high polarity functional groups like amines) because they must be soluble in aqueous liquids like blood, and water has a high solubility parameter. So, the direction has been to less hydrophilic, more hydrophobic, polymers to avoid the possibility of the therapeutic agents partially dissolving in a medium solubility parameter, medium polarity, polyester, and thus be more fully available in the serum phase for analysis. Imparting hydrophobic character to the polyester has been done via two main techniques. Firstly, a random copolymer has been made of a diol and large quantities of a dicarboxylic acid with pendent, long ($C_9$ to $C_{13}$) olefin groups. Secondly, a random copolymer has been made of a diol and large quantities of a dicarboxylic with a long olefin along its backbone, such as a $C_{36}$ dimerized fatty acid. Such polyester compositions have proved useful as functional blood partitioning compositions having reduced affinity for therapeutic agents present in blood such as phenobarbital and imipramine. See, for example, W. L. O'Brien, U.S. Pat. No. 5,124,434, the entire disclosure of which is incorporated by reference in the present specification, as if set forth herein in full.

SUMMARY OF THE INVENTION

In accordance with the present invention, fluid compositions have been discovered that are resistant to penetration by therapeutic agents, they comprise $\alpha$-olefin terminated polyesters and polymerized $\alpha$-olefins in which the components form a stable continuous phase due to the compatibilization action of the $\alpha$-olefin terminated polyester. The invention is also the use of the fluids for physiological separations and a process for making the fluids. The fluids can be made with olefin content, and hence hydrophobicity, as high as that contained in the random copolymer polyesters shown to work as therapeutic agent barriers in the past, but a significant portion of the olefin content is as a mixed in polymerized $\alpha$-olefin; an advantage being that polymerized $\alpha$-olefins are commodity items that are more economical than custom polyesters.

About 1 to about 5% $\alpha$-olefin terminated polyester is mixed with conventional polyester and this then forms compatible mixtures with about 1 to about 20% polymerized $\alpha$-olefins.

The fluids of the invention are readily formulated together with other ingredients, typically a suitable filler, such as silica, and compatible surfactant or other coupling agent, into functional blood partitioning compositions, as is well known in the art. The density of the finished blood partitioning composition is controlled within prescribed limits, so that during centrifugation the composition becomes stably positioned at the interface between the serum or plasma phase and heavier cellular phase and, when centrifugation is terminated, forms a continuous integral barrier within the blood collection vessel to prevent the two phases from recombining or mixing, especially when decanting or pipetting the serum or plasma. The blood partitioning compositions of the invention are advantageously employed in small amounts, on the order of 1-5 g., in a 10 ml blood collection vessel of the type previously described which are then ready for use in blood sampling and analysis in the usual way. The polyester-based blood partitioning compositions of the invention are especially suited for use in TDM procedures.

DETAILED DESCRIPTION OF THE INVENTION

An embodiment of the invention is $\alpha$-olefin terminated polyesters capable of forming a stable continuous phase with polymerized $\alpha$-olefins due to the compatibilization action of the $\alpha$-olefin terminated polyesters. This allows olefin contents as high as those obtained with the high-olefin random copolymer approaches heretofore used to achieve low therapeutic agent absorption, but with a substantial formulating fraction of an ingredient, polymerized $\alpha$-olefins, that is more economical than custom polyesters. As will be seen in example 1 below, even when a polyester contains a dimerized fatty acid, the polyester does not form a stable mixture with polymerized $\alpha$-olefins, but when small amounts of olefin-terminated polyester are present or when a functionalized polyolefin is used as a reactant to form the polyester, a wide range of stable mixtures with polymerized $\alpha$-olefins becomes available. Analogous devices have been used to facilitate polymer alloying, involving components which differ markedly in molecular structure and crystallinity so that if heated, molded and cooled they would form distinct domains apart from one another, rendering production of useful articles impossible.

One such pair of incompatible materials is isotactic polypropylene and nitrile rubber; the coupling of these polymers was accomplished by incorporating ~0.5% of a product derived from hydrogenated nitrile rubber (nitrile →amine) and maleated PP, generated in situ as a mixture of imide and succinamic acid. (A. Y. Coran and R. Patel, Rubber Chem. Technol., 56, 1045 (1983).

The olefin terminated polyester is made by first making certain that the polyester is substantially hydroxyl-terminated on both ends, then reacting this intermediate with a functionalized $\alpha$-olefins, the function selected to be reactive with the hydroxyl-terminations. The "ene" group of the selected $\alpha$-olefin is preferentially reacted with maleic anhydride or acrylonitrile. An example of an $\alpha$-olefin that may be used is 1-dodecene. When reacted with maleic anhydride it forms dodecenyl succinic anhydride. One mole of dodecenylsuccinic anhydride is then reacted with each mole of hydroxyl on the polyester. Note that there may be more than two moles of hydroxyl per polyester chain as commercial "dimerized" fatty acids can contain trimerized species leading to branched polyesters, which this invention includes.

An outline of the typical steps then to make the invention would typically look like: 1) react carboxylic acids with sufficient diol to achieve an acid value $\leq 7$ with a hydroxyl value of about 40. 2) Introduce an ester interchange catalyst and remove volatile diol until the desired hydroxyl value and viscosity are observed. 3) Treat a portion of the substantially hydroxy terminated polyester thus obtained with one mole of functionalized olefin, as exemplified by any of the alkenylsuccinic anhydrides available commercially. 4) The product obtained by step 3 is used at 1-5% to compatibilize the polyester/poly-$\alpha$-olefin mixture.

As an alternative to the foregoing, formulations containing alkenylsuccinic anhydride as about 5 to about 20 equivalents % of the dibasic acid may be used to form polyesters directly as in steps 1 and 2, above. The resulting polyesters also exhibit increased compatibility with poly-$\alpha$-olefin.

The details of the fluids, ingredients and process will now be discussed.

The fluids according to the invention are produced in the form of viscous liquids, having a specific gravity at room temperature in the range of 1.015-1.09 and preferably from about 1.02 to about 1.035.

Particularly notable among the properties of these fluids is their inertness, making them especially useful in TDM programs. The polyesters of the invention are also highly hydrophobic, exhibiting negligible water solubility. The Hoy solubility parameter is about equal to or less than 9. The physical and chemical properties of these polyesters are uniformly maintained over extended periods prior to use, as well as during transportation and processing of blood samples.

The intermediate hydroxyl-terminated polyesters of the invention are characterized by having an acid value of about 2 or less, an hydroxyl value of about 30 or less, but greater than 5, and a 100° C. kinematic viscosity of about 1700–4000 centistokes. The finished fluids of the invention will typically have a viscosity greater than, or equal to, 2000 cSt, and preferably greater than, or equal to, 3000 cSt, when measured at 100° C. or a viscosity of from about 3000 to about 4000 cSt.

Fluids having the above-described properties are especially useful as blood partitioning agents in blood collection vessels where they provide a continuous integral barrier or seal between the serum and clot portions of blood. In other words, the fluid completely partitions the separated phases so that the serum and cellular or clot portions are no longer in contact at any point, forming a unitary seal which firmly adheres to the inner surface of the blood collection vessel. By forming a continuous, integral barrier in this way, it is possible to easily remove the serum or plasma portion by decanting or pipetting, with the clot portion remaining undisturbed in the collection vessel.

The dicarboxylic acid member of the α-olefin terminated polyesters is primarily selected for economy in achieving the selected properties and the optimal choice may depend on market value. However, typical candidate diacids include: adipic acid, phthalic anhydride, dodecanedioic acid, dodecenylsuccinic acid, succinic acid, glutaric acid, pimelic acid, suberic acid, azelaic acid, sebacic acid, undecanedioic acid, terephthalic acid, isophthalic acid, dimerized fatty acids or mixtures thereof. Dimerized fatty acids are also known as polymerized fatty acids, which include aliphatic dicarboxylic acids having from about 32–40 carbon atoms obtained by the polymerization of olefinically unsaturated monocarboxylic acids having from 16–20 carbon atoms, such as palmitoleic acid, oleic acid, linoleic acid, linolenic acid and the like. Polymeric fatty acids and processes for their production are well known. See, for example, U.S. Pat. Nos. 2,793,219 and 2,955,121. Polymeric fatty acids particularly useful in the practice of this invention preferably will have as their principal component C-36 dimer acid. Such C-36 dicarboxylic acids are obtained by the dimerization of two moles of a C-18 unsaturated monocarboxylic acid, such as oleic acid or linoleic acid, or mixtures thereof, e.g., tall oil fatty acids. These products typically contain 75% by weight or more of C-36 dimer acid and have an acid value in the range of 180–215, saponification value in the range of 190–215 and neutral equivalent from 265–310. Examples of commercial dimer acids of this type are EMPOL® 1008, EMPOL® 1015, EMPOL® 1061, EMPOL® 1016, EMPOL® 1018, EMPOL® 1022 and EMPOL® 1024, all trademarked products of the Henkel Corporation, and identified hereinafter as a class as "C-36 dimer acid." The dimer acids may be hydrogenated prior to use. To increase the C-36 dimer content and reduce the amount of by-product acids, including unreacted monobasic acid, trimer and higher polymer acids, the polymeric fatty acid may be molecularly distilled or otherwise fractionated. EMPOL® 1016, used in the examples below, is a typical C-36 dimer acid and has an acid value in the range from about 190 to about 198 and a saponification value of about 197.

It will be apparent to those skilled in the art that the various art-recognized equivalents of the aforementioned dicarboxylic acids, including anhydrides and lower alkyl esters thereof, may be employed in preparing the polyesters of the invention. Accordingly, as used herein, the term "acid" is intended to encompass such acid derivatives. Methyl esters are particularly advantageous for the preparation of the polyesters described herein. Mixtures of acids, anhydrides and esters may also be reacted to obtain the desired product.

Suitable diols which may be reacted with the above described dicarboxylic acid(s) to yield the polyesters of the invention include diols of the formula:

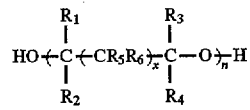

in which $R_1$, $R_2$, $R_3$ and $R_4$ are independently selected from the group consisting of hydrogen and an alkyl group having 1–4 carbon atoms, n=1–4 and x=0–4. Representative diols falling within the foregoing formula include ethylene glycol, neopentylglycol, 1,3-butanediol, 1,4-butanediol, propylene glycol, diethylene glycol, triethylene glycol, 1,2-butanediol, 3-methyl-1,5-pentanediol, 1,2-pentanediol, 1,3-pentanediol, 1,4-pentanediol, 1,5-pentanediol, hexylene glycol, 1,6-hexanediol, polytetramethylene ether diol, cyclohexanedimethanol, benzenedimethanol, polyoxypropylene diol, dipropylene glycol, trimethylpentanediol, propoxylated bisphenol A, 1,4-Bis(2-hydroxyethoxy)benzene, tetramethylene adipate glycol, polycaprolactone glycol, polyhexamethylenecarbonate glycol, 1,6-hexanediol and hydrogenated bisphenol A and the like and mixtures thereof. The preferred diols contain from 3–5 carbon atoms, with particularly useful polyester products being obtained using neopentyl glycol, propylene glycol, triethylene glycol, or mixtures thereof. In a particularly preferred embodiment of the invention, in which a mixture of neopentyl glycol and propylene glycol is used, the amount of neopentyl glycol comprises about 70 to about 95 equivalent percent, and the amount of propylene glycol comprises about 5 to about 30 equivalent percent of the total diol component equivalents.

If an improvement in color is desired, the polyester may be bleached by any of the well known and acceptable bleaching methods, e.g., using hydrogen peroxide or chlorite. Alternatively, the polyester may be decolorized by filtering through a filter aid, charcoal or bleaching clay.

The rate of esterification may be enhanced by the use of known esterification catalysts. Suitable esterification catalysts for enhancing the rate of esterification of free carboxyl groups include phosphoric acid, sulfuric acid, toluenesulfonic acid, methane sulfonic acid, and the like. The amount of such catalyst may vary widely, but most often will be in an amount from about 0.1% to about 0.5% by weight, based on the total reactant charge. Catalysts useful for effecting ester interchange include dibutyltin diacetate, stannous oxalate, dibutyltin oxide, tetrabutyl titanate, zinc acetate and the like. These catalysts are generally employed in an amount ranging from about 0.01% to 0.05% by weight, based on the total reactant charge. When such a catalyst is used, it is not necessary that it be present throughout the entire reaction. It is sometimes advantageous in order to obtain products having good color and relatively low acid value, on the order of 2 mg KOH/g, or less for the hydroxyl-terminated precursor, to add the catalyst during the final stages of the reaction. Upon completion of the reaction, the catalyst may be deactivated and removed by filtering or left in place, as is commonly done.

To prepare the hydroxy-terminated polyester, a small excess (based on the equivalents of acid present) of a volatile diol may used. The excess diol also serves as the reaction medium and reduces the viscosity of the reaction mixture. The excess diol is distilled off as the esterification is carried to completion and may be recycled to the reactor if desired. Generally, about 20% by weight excess volatile diol, based on the total weight of the diol component, will suffice. Where a volatile and a relatively involatile diol are present together, any excess is supplied as additional volatile diol. The more volatile glycols are commonly used for this purpose. Among them are propylene glycol, ethylene glycol, 1,3- butanediol, 1,4-butanediol, 1,2-butanediol, 3-methyl-1, 5-pentanediol and the like.

The functionalized α-olefin is made by reacting the "ene" of an α-olefin with a reagent that renders the α-olefin reactive with hydroxyl groups, among these reagents are maleic anhydride and acrylonitrile and the like. This reaction may be carried out in the presence of a catalyst, and is well known in the art. Commercially available α-olefins generally range from $C_{12}$ to $C_{76}$, but α-olefins outside this range would also be expected to work as well. When reacted with maleic anhydride, as a class they form olefin succinic anhydrides, which will react with the terminal hydroxyls in substantially equimolar ratio to form terminal olefins. In weight percent for the molecular weight ranges commonly found in the polyesters, the use level is about 1 to about 5%.

The polymerized α-olefins, also known as α-polyolefins are substantially inert oily liquids. They are generally, but not necessarily, atactic in structure. Examples are polypropylene, polybutene, propylene-ethylene copolymers, propylene-butene copolymers, polypropylene/propylene-ethylene copolymer mixtures, polypropylene-butene-ethylene terpolymer, octene copolymers, EMERY® 3008, which is poly-1-decene, maleated EMERY® 3008 and the like. Note that any oil with a solubility parameter similar to that of the polymerized α-olefins would be expected to be compatibilized by the olefin-terminated polyester. Typically, about 1 to about 20 weight% is added to the olefin terminated polyester to achieve the desired density and solubility parameter.

Almost all therapeutic agents are designed to have high solubility parameters, in order to be soluble in bodily fluids and tissue, which are primarily aqueous-based. Since like dissolves like, the high-olefin, low solubility parameter fluids of the invention, and the prior art, resist their penetration. Therapeutic agents as a class, and this is not meant to be limiting, that have been shown to have limited penetration are amines and tricyclic amine anti-depressants. Examples of tricyclic amines include imipramine, desipramine, amitriptyline, amoxapine, doxepin, nortriptyline, protriptyline, trimipramine and their pharmacologically acceptable salts. Other therapeutic agents that find fluids of this sort to be barriers come from classes as diverse as sedatives, anti-neoplastics, topical anesthetics, cardiac drugs and anti-asthmatics; examples include phenobarbital, phenytoin, methotrexate, digoxin, lidocaine, theophylline and their pharmacologically acceptable salts.

A first particularly useful polyester precursor is obtained by reacting a total of 1.0 mole of acid member which is comprised of about 0.887 equivalent adipic acid, about 0.113 equivalent EMPOL® 1016 dimer acid with about 1.0 mole of diol member comprising neopentyl glycol and propylene glycol. The equivalents ratio of neopentyl glycol to propylene glycol ranges from about 0.75:0.25 to about 0.90:0.10. The reactor charge also includes about a 20% molar excess, based on diol, of volatile diol to obtain the hydroxyl-terminated diol, the excess diol being stripped.

A second particularly useful polyester precursor is obtained by reacting a total of 1.0 mole of acid member which is comprised of about 0.8957 equivalent azelaic acid, about 0.1043 equivalent EMPOL® 1016 dimer acid with about 0.9 eq. neopentyl glycol and 0.3 eq. propylene glycol of which about 0.2 is excess and is mostly removed. The specific gravity of the polyester is about 1.022 to about 1.026 when measured at 25° C. and the viscosity is from about 3050 to about 3500 cSt when measured at 99° C.

The source of the acids or acid derivatives and the manner by which the dicarboxylic acid blends are prepared, in those embodiments where such blends are used, is of no consequence so long as the resulting blend contains the specified acids or acid derivatives in the required ratios. Thus, dicarboxylic acid or acid derivative blends may be obtained by mixing the individual acid components. On the other hand, mixtures of acid obtained as by-products from various manufacturing operations and which contain one or more of the necessary acid components may be advantageously utilized. For example, mixed dimethyl esters of succinic, glutaric and adipic acids may be obtained as a co-product from the manufacture of adipic acid and may be conveniently blended with any other acid, e.g., oleic dimer acid selected for inclusion in the polyester of the invention.

Preparation of blood partitioning compositions using the polyesters of the invention may be carried out in the manner described in commonly owned U.S. Pat. Nos. 4,101,422 and 4,148,764, the entire disclosures of which are incorporated by reference in the present specification, as if set forth herein in full.

Determination of the extent of interaction between the polyesters of the invention and commonly monitored drugs may be carried out using well known recovery experiments and drug measurement techniques, such as, gas chromatography, gas-liquid chromatography, high-performance liquid chromatography, thin layer chromatography or immunoassay techniques, including radioimmunoassay, enzyme immunoassay, fluorescence polarization immunoassay, nephelometric assay, and the like. A variety of suitable procedures are reported in the literature. See, for example, Bergquist et al., supra. Such determinations may be carried out using human serum, or commercially available bovine serum, if desired.

The following examples are presented to illustrate the invention more fully, and are not intended, nor are they to be construed, as a limitation of the scope of the invention. In the examples, all percentages are on a weight basis unless otherwise indicated.

The first example is a control illustrating the phase separation that occurs when a polyester, even one containing dimer acid is mixed with a polymerized α-olefin. Example 2 shows direct formation of a compatibilization polyester and the compatible mixture with a poly (α-olefin). Examples 3 and 4 describe syntheses of two additional olefin-terminated polyester embodiments of the invention These are. Example 5 shows the olefin-terminated polyesters of Examples 3 and 4 being used as compatibilizers to mix the second preferred polyester described above with a poly (α-olefin). Example 5 also shows the addition of silica and couplers to the compatibilized mixture of olefin-terminated polyester, polyester and poly (α-olefin) to form a useful material for isolation of serum.

EXAMPLE 1

The second preferred polyester described above was mixed with maleated (about 0.3% maleated) penta-1-decene at 9:1 ester/olefin ratio and failed to form a clear mixture on standing after thorough mixing and remained so for 60 days; the olefin was decantable.

EXAMPLE 2

A reactant charge was prepared for a one-pot synthesis, including 0.91 equivalent adipic acid, 0.09 eq. $C_{76}$ succinic anhydride, 0.3 equivalent propylene glycol, and about 0.9 equivalent neopentyl glycol. The polyester recovered had an acid value of less than or equal to 1.5 mg KOH/g, an hydroxyl value of less than or equal to 22.5, 210° F. kinematic viscosity of 3000–3850 cSt and a specific gravity at 25° C. of 1.0342. This was mixed with penta-1-decene; the resulting fluid was clear and homogenous immediately after mixing and remained so after standing for 60. An azelate analog was also prepared using 0.95 eq. EMEROX® 1110 azelaic acid and 0.05 eq. $C_{76}$ succinic anhydride, specific gravity 1.0254.

EXAMPLE 3

A reactant charge was prepared, including 0.887 equivalent adipic acid, 0.113 equivalent EMPOL® 1016 dimer acid, 0.1 equivalent propylene glycol, and about 0.9 equivalent neopentyl glycol. This was then reacted with about a 20% molar excess, based on diol, of propylene to obtain the hydroxyl-terminated diol, the excess diol being stripped. The catalyst in the final stage was di-n-butyltin diacetate 0.03% based on metal content. The substantially hydroxyl-terminated polyester recovered had an acid value of less than or equal to 1.5 mg KOH/g, an hydroxyl value of 20, 210° F. kinematic viscosity of 3000–3850 cSt and a specific gravity at 25° C. of 1.052–1.056. 280.5 g (0.1 eq.) of this polyester was charged into a 500 ml thermostated reaction flask with drying tube along with 56.1 g (0.1 eq.) $C_{76}$ polyisobutenyl succinic anhydride. At t=0, and T=25° C., the thermostat was set to 95° C. At t=25 min., T=70° C., the viscosity had dropped and agitation was started. At t=35 min., T=94° C. and turbidity had developed in the heavy phase. At t=75 min., T=98° C. and the upper phase was almost gone. At t=210 min., T=98° C. and a 1.3 ml aliquot was removed and found to have an acid value of 8.6, the reaction being essentially complete. At t=360 min., T=98° C., the heat was turned off, the resulting olefin-terminated polyester was a honey-like, turbid syrup; no separation was seen.

EXAMPLE 4

A polyester as in example 3 was prepared with a resulting hydroxyl number of 20. 280.5g (0.1 eq.)of this polyester was charged into a 500 ml thermostated reaction flask with drying tube along with 15 g (0.1 eq.) dodecenyl succinic anhydride. At t=0, and T=25° C., the thermostat was set to 95° C. At t=30 min., T=96° C., the thermostat was increased to 100° C. At t=150 min., T=100° C. and turbidity development was not seen. At t=360 min., T=100° C., the product was poured out while warm. The resulting was amber, clear and had no phase separation. It had a acid value of 10.356.

EXAMPLE 5

The olefin-terminated polyesters of Ex. 3 and 4 were mixed with unmodified precursor polyester of Examples 3 and 4 in the ratio 1 part per alkenylsuccinic anhydride: 99 precursor polyester; addition of 10 parts per penta-1-decene to 90 of the foregoing mixture gave a homogeneous clear solution in the case where the adduct of ex. 4 was used, and a turbid mixture in the case of ex. 3. Neither exhibited separation of the light polyolefin component after 4 months @25°–30° C. About 8 wt. % poly-1-decene achieves a density equal to that of the second preferred polyester, whence addition of about 4% silica and couplers results in a specific gravity of about 1.045 to about 1.047, a useful density for the isolation of serum from whole blood.

While the present invention has been described and exemplified above in terms of certain preferred embodiments, various other embodiments may be apparent to those skilled in the art. Accordingly, the invention is not limited to the embodiments specifically described and exemplified, but variations and modifications may be made therein and thereto without departing from the spirit of the invention, the full scope of which is delineated by the following claims.

What is claimed is:

1. A fluid composition for physiological separations that is resistant to penetration by therapeutic agents, which comprises an α-olefin terminated polyester and an unmodified polyester.

2. A fluid in accordance with claim 1, said α-olefin terminated polyester being formed in-situ by reaction of a functionalized α-olefin with said unmodified polyester.

3. A fluid in accordance with claim 1, said α-olefin terminated polyester being separately synthesized from a substantially hydroxyl-terminated polyester and a functionalized α-olefin.

4. A fluid in accordance with claim 1, further comprising a polymerized α-olefin.

5. A fluid in accordance with claim 4, wherein the polymerized α-olefin is from about 1 to about 20% by weight of the fluid.

6. A fluid in accordance with claim 4, wherein the polymerized α-olefin is poly-1-decene.

7. A fluid in accordance with claim 4, wherein the polymerized α-olefin is penta-1-decene.

8. A fluid in accordance with claim 4, wherein the polymerized α-olefin is maleated poly-1-decene.

9. A fluid in accordance with claim 1, further comprising silica.

10. A fluid in accordance with claim 1, further comprising a coupling agent.

11. A fluid in accordance with claim 1, wherein the fluid has a specific gravity of about 1.015 to about 1.09 and preferably from about 1.02 to about 1.035.

12. A fluid in accordance with claim 1, wherein the fluid has a Hoy solubility parameter less than about 9.

13. A fluid in accordance with claim 2, wherein the functionalized α-olefin is used at a treat level of about 1 to about 5% to form a compatibilizer in place, whereby stable mixtures with unmodified polyester fluids containing up to about 20% of poly-α-olefin may be formed.

14. A fluid in accordance with claim 2, wherein the functionalized α-olefin is an α-olefin reacted with maleic anhydride.

15. A fluid in accordance with claim 2, wherein the functionalized α-olefin is prepared from an α-olefin of from about $C_{12}$ to about $C_{76}$.

16. A fluid in accordance with claim 2, wherein the unmodified polyester is aliphatic.

17. A fluid in accordance with claim 2, wherein the unmodified polyester comprises at least one dicarboxylic acid and at least one diol.

18. An unmodified polyester in accordance with claim 15, wherein the dicarboxylic acid is selected from the group consisting of adipic acid, phthalic anhydride, dodecanedioic acid, dodecenylsuccinic acid, succinic acid, glutaric acid, pimelic acid, suberic acid, azelaic acid, sebacic acid, undecanedioic acid, terephthalic acid, isophthalic acid, dimerized fatty acids and mixtures thereof.

19. An unmodified polyester in accordance with claim 17, wherein said diol has the general formula

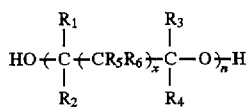

in which R1, R2, R3, R4, R5 and R6 are independently selected from the group consisting of hydrogen and alkyl having 1–4 carbon atoms, n=1–4 and x=0–4.

20. An unmodified polyester in accordance with claim 17, wherein the diol is selected from the group consisting of ethylene glycol, neopentylglycol, 1,3-butanediol, 1,4-butanediol, propylene glycol, diethylene glycol, triethylene glycol, 1,2-butanediol, 3-methyl-1,5-pentanediol, 1,2-pentanediol, 1,3-pentanediol, 1,4-pentanediol, 1,5-pentanediol, hexylene glycol, 1,6-hexanediol, polytetramethyleneetherdiol, cyclohexanedimethanol, benzenedimethanol, polyoxypropylene diol, dipropylene glycol, trimethylpentanediol, propoxylated bisphenol A, 1,4-Bis(2-hydroxyethoxy)benzene, tetramethylene adipate glycol, polycaprolactone glycol, polyhexamethylenecarbonate glycol, 1,6-hexanediol and hydrogenated bisphenol A or a mixture thereof.

21. A fluid in accordance with claim 2, wherein the fluid comprises $C_{76}$ succinic anhydride, adipic acid, propylene glycol, and neopentyl glycol.

22. A fluid in accordance with claim 2, wherein the fluid nominally comprises about 0.09 eq.$C_{76}$ succinic anhydride, about 0.91 eq. adipic acid, about 0.1 eq. propylene glycol, and about 0.9 eq. neopentyl glycol.

23. A process for making a fluid for physiological separations that is resistant to penetration by therapeutic agents, which comprises reacting at least one alkenyl succinic anhydride with at least one diol and at least one diacid to form a mixture of olefin terminated polyester and unmodified.

24. A process for making a fluid in accordance with claim 23, which further comprises mixing in a polymerized α-olefin, whereby the components form a stable continuous phase due to the compatibilization action of said α-olefin-terminated polyester.

25. A fluid in accordance with claim 3, wherein the α-olefin terminated polyester is used at a treat level of about 1 to about 5% to form a compatibilizer in place, whereby stable mixtures with unmodified polyester fluids containing up to about 20% of poly-α-olefin may be formed.

26. A fluid in accordance with claim 3, wherein the ratio of functionalized α-olefin is about equimolar to the hydroxyl-terminated polyester, based on hydroxyl and the resulting product is mixed with unmodified polyester at a treat level of about 1 to about 5% to form a compatibilizer in place, whereby stable mixtures with conventional polyester fluids containing up to about 20% of poly-α-olefin may be formed.

27. A fluid in accordance with claim 3, wherein the functionalized α-olefin is an α-olefin reacted with maleic anhydride.

28. A fluid in accordance with claim 3, wherein the functionalized α-olefin is prepared from an α-olefin of from about $C_{12}$ to about $C_{76}$.

29. A fluid in accordance with claim 3, wherein the hydroxyl-terminated polyester has a viscosity of from about 500 cSt to about 4500 cSt.

30. A fluid in accordance with claim 3, wherein the hydroxyl-terminated polyester has hydroxyl number greater than about 5 and less than about 30.

31. A fluid in accordance with claim 3, wherein the hydroxyl-terminated polyester is aliphatic.

32. A fluid in accordance with claim 3, wherein the hydroxyl-terminated polyester comprises at least one dicarboxylic acid and at least one diol.

33. A hydroxyl-terminated polyester in accordance with claim 32, wherein the dicarboxylic acid is selected from the group consisting of adipic acid, phthalic anhydride, dodecanedioic acid, dodecenylsuccinic acid, succinic acid, glutaric acid, pimelic acid, suberic acid, azelaic acid, sebacic acid, undecanedioic acid, terephthalic acid, isophthalic acid, dimerized fatty acids or a mixture thereof.

34. A hydroxyl-terminated polyester in accordance with claim 32, wherein said diol has the general formula

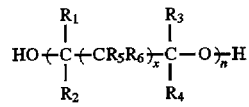

in which R1, R2, R3, R4, R5 and R6 are independently selected from the group consisting of hydrogen and alkyl having 1–4 carbon atoms, n=1–4 and x=0–4.

35. A hydroxyl-terminated polyester in accordance with claim 32, wherein the diol is selected from the group consisting of ethylene glycol, neopentylglycol, 1,3-butanediol, 1,4-butanediol, propylene glycol, diethylene glycol, triethylene glycol, 1,2-butanediol, 3-methyl-1,5-pentanediol, 1,2-pentanediol, 1,3-pentanediol, 1,4-pentanediol, 1,5-pentanediol, hexylene glycol, 1,6-hexanediol, polytetramethyleneetherdiol, cyclohexanedimethanol, benzenedimethanol, polyoxypropylene diol, dipropylene glycol, trimethylpentanediol, propoxylated bisphenol A, 1,4-Bis(2-hydroxyethoxy)benzene, tetramethylene adipate glycol, polycaprolactone glycol, polyhexamethylenecarbonate glycol, 1,6-hexanediol and hydrogenated bisphenol A or a mixture thereof.

36. A fluid in accordance with claim 3, wherein the functionalized α-olefin comprises dodecenyl succinic anhydride and the polyester comprises adipic acid, C-36 dimer acid, propylene glycol, and neopentyl glycol.

37. A fluid in accordance with claim 3, wherein the functionalized α-olefin comprises dodecenyl succinic anhydride and the polyester, in equimolar amount based on hydroxyl, nominally comprises, about 0.887 adipic acid, about 0.113 C-36 dimer acid, about 0.1 propylene glycol, and about 0.9 neopentyl glycol.

38. A fluid in accordance with claim 3, wherein the functionalized α-olefin comprises $C_{76}$ polyisobutenyl succinic anhydride and the polyester comprises adipic acid, C-36 dimer acid, propylene glycol, and neopentyl glycol.

39. A fluid in accordance with claim 3, wherein the functionalized α-olefin comprises $C_{76}$ polyisobutenyl succinic anhydride and the polyester, in equimolar amount based on hydroxyl, nominally comprises about 0.887 adipic acid, about 0.113 C-36 dimer acid, about 0.1 propylene glycol, and about 0.9 neopentyl glycol.

40. A process for making a fluid for physiological separations that is resistant to penetration by therapeutic agents, which comprises:

reacting substantially equimolar amounts of a diol and a dicarboxylic acid to form a polyester, with sufficient excess volatile diol present to assure that the polyester formed is predominantly hydroxyl terminated;

stripping excess said volatile diol; and reacting said hydroxyl-terminated polyester with a functionalized α-olefin to form a substantially α-olefin-terminated polyester.

41. A process for making a fluid in accordance with claim 40, which further comprises mixing said α-olefin-terminated polyester with an unmodified polyester.

42. A process for making a fluid in accordance with claim 41, which further comprises mixing in a polymerized α-olefin, whereby the components form a stable continuous phase due to the compatibilization action of said α-olefin-terminated polyester.

* * * * *